United States Patent
Jeter et al.

(10) Patent No.: US 8,532,256 B1
(45) Date of Patent: Sep. 10, 2013

(54) METHOD AND APPARATUS FOR THE AUTOMATED ASSAY AND VALUATION OF PRECIOUS METAL OBJECTS

(76) Inventors: Bobby D. Jeter, Sandwich, IL (US); John Bosjancic, Joliet, IL (US)

( * ) Notice: Subject to any disclaimer, the term of this patent is extended or adjusted under 35 U.S.C. 154(b) by 5 days.

(21) Appl. No.: 13/385,734

(22) Filed: Mar. 5, 2012

(51) Int. Cl.
 *G01N 23/223* (2006.01)
(52) U.S. Cl.
 USPC ............................................. 378/48; 378/45
(58) Field of Classification Search
 USPC ..................................... 378/44–50
 See application file for complete search history.

(56) References Cited

U.S. PATENT DOCUMENTS

| 5,062,127 | A | | 10/1991 | Sayama et al. | |
| 5,418,826 | A | * | 5/1995 | Sato et al. | 378/48 |
| 6,370,220 | B1 | * | 4/2002 | Stoop | 378/45 |
| 6,765,986 | B2 | * | 7/2004 | Grodzins et al. | 378/46 |
| 2008/0015870 | A1 | * | 1/2008 | Elowitz et al. | 705/1 |

* cited by examiner

*Primary Examiner* — Hoon Song

(57) ABSTRACT

A method and apparatus for the metallurgical qualitative analysis (assay) and valuation of precious metals objects such as jewelry or coins. The system integrates a commercially available x-ray florescence (XRF) metals analyzer with associated peripheral devices including a personal computer and keyboard or touchpad computing device, a digitizing scale, a printer, an Internet link for obtaining current precious metals market price quotations, and software for processing the qualitative results with the current market price data and presenting the results to the system operator in real time. The system optionally includes a customer interface including a display screen for presenting the customer with the results of the analysis and valuation, and customer input means for accepting and recording a purchase transaction.

8 Claims, 2 Drawing Sheets

Figure 1:
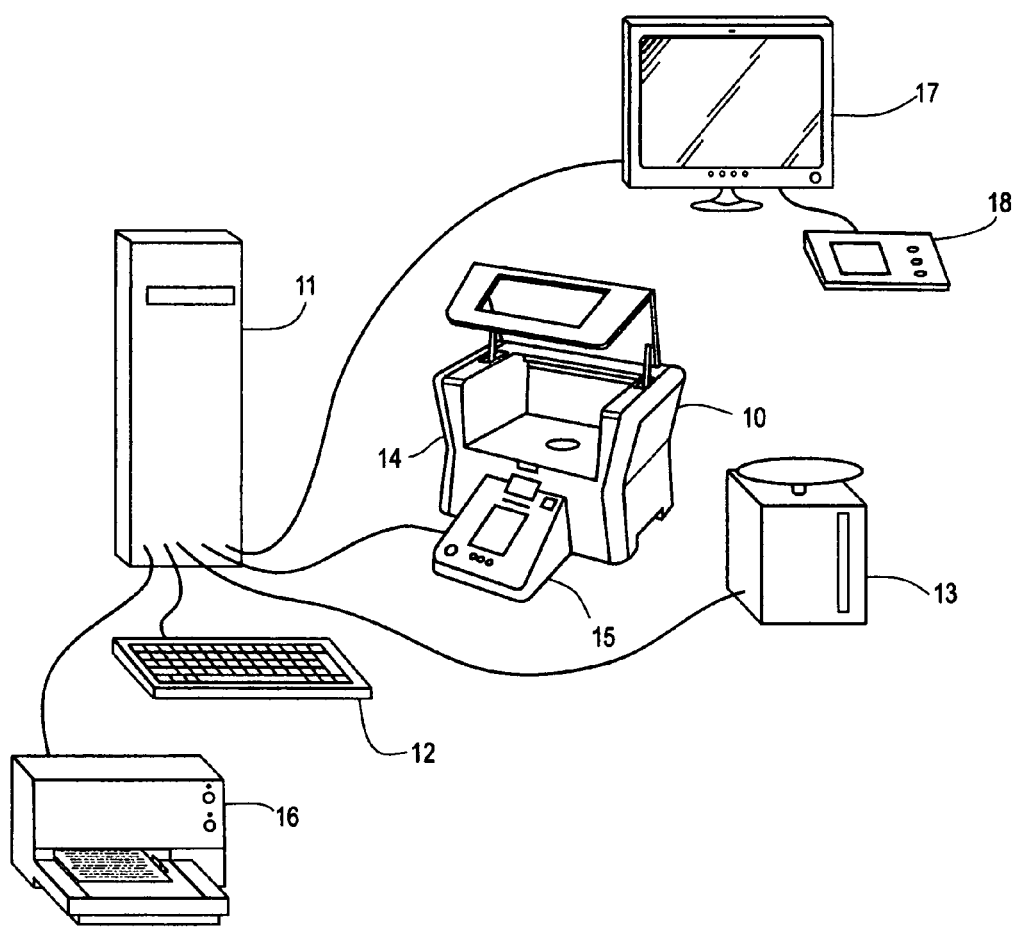

METHOD AND APPARATUS FOR THE AUTOMATED ASSAY AND VALUATION OF PRECIOUS METAL OBJECTS

FIELD OF THE INVENTION

The present invention pertains to an integrated "all-in-one" method and apparatus for the metallurgical qualitative analysis (assay) and valuation of precious metals objects such as jewelry or coins. The system combines a commercially available metals analyzer with specialized electronic controls and a novel "artificial intelligence" software to provide a method and apparatus that can be operated rapidly and with consistent results even by an inexperienced user. The invention is particularly useful for the appraisal and valuation of jewelry and other precious metal articles by gold buyers, jewelry stores, pawn shops, and similar users who require a quick, accurate, non-destructive and inexpensive means of performing on-site analysis and appraisal of precious metals in a retail environment.

BACKGROUND OF THE INVENTION

There is presently an increasing demand for a means to quickly and accurately assay jewelry, coins and other precious metals in a retail environment.

Conventionally, such articles were appraised using the so-called "touchstone method", an age-old technique that is relatively nondestructive to jewelry and offers quick results. Touchstone testing is based on the fact that 24k gold resists all but the strongest acids. However, since this method necessarily uses one or more acids, close attention to safety and careful procedures are a must.

In practicing this method, a portion of the article to be tested is rubbed against a black quartz test stone whereby an elemental deposit is obtained on the test stone which is then treated with one or more acids, by which the metallic composition of the test article is determined. To be properly performed, the touchstone method requires a certain level of skill and experience, and necessarily tends to mar the article being tested. Additionally, this test is not as effective on some alloys such as white gold (gold-palladium alloys) and platinum alloys which are significantly harder, nor to significantly softer materials such as fine gold, or certain other alloys containing more than 92% gold.

OTHER PRIOR ART

In addition to the touchstone method described above, other prior art assay techniques include: measurement of specific gravity, the "fire assay method", atomic absorption spectrometry, and inductively coupled plasma spectrometry (ICP). However, each of these methods has drawbacks and problems which render it impractical for accurate appraisal performed at a retail place of business where speed and efficiency are critical for making a "buy/do-not-buy" decision. Each of these prior art methods has significant disadvantages.

While a determination of specific gravity can be easily performed by measuring the weight of the subject article while suspended in water, this method cannot be used to determine the metallic content of the unknown sample. The fire assay method, atomic absorption spectrometry and inductively coupled plasma spectrometry are all destructive methods and can therefore not be used on articles for sale.

The use of conventional equipment for fluorescence X-ray spectrometry requires that the assay sample be homogeneous, with at least one flat and even surface. Choosing the best point on the sample to direct the X-ray beam is difficult because with conventional equipment the X-ray beam is of a relatively large diameter (20 mm or greater). Therefore small specimens having a complex structure, or specimens made up of a number of different alloys, cannot be reliably assayed with such devices. Furthermore, conventional fluorescence X-ray spectrometry equipment is generally quite large and expensive, occupying more space and requiring more specialized knowledge than most retail operations can provide.

In general, the analysis of precious metals by such conventional prior art acid and/or x-ray technology requires a vast amount of knowledge and experience not just to obtain the data, but also to accurately interpret the results. For example, many heavily plated materials (such as gold and silver jewelry) can fool even experienced precious metals buyers as to their true make-up, causing the buyer to offer more than what the specimen is actually worth, in addition to requiring considerable time and operator experience to obtain reliable results.

THE OBJECTIVES OF THE INVENTION

The present invention utilizes a relatively recent advance in the prior art, namely, the commercially available XRF (X-ray florescence) analyzing tester marketed by several manufacturers such as Olympus Corporation's "Innov-x" product, Thermo Scientific, Bruker AXS (A division of Bruker Corporation), among others (not named). Such X-ray florescence apparatus is believed to utilize the technology disclosed by Sayama, et al., U.S. Pat. No. 5,062,127 (Oct. 29, 1991), assigned to Mitsubishi Metal Corp.

The commercial embodiments offered by the above-mentioned companies have achieved a significant advantage over the largely manual assay techniques of the prior art. As correctly envisioned by the Sayama, et al. inventors, the process disclosed in U.S. Pat. No. 5,062,127 can be nearly totally automated. However, this patent does not disclose or suggest how this can advantageously be done, either alone or in combination with other data, such as current market price, digitally captured weight of the subject item or a digital photographic image of the object, which is the principal object of the present invention.

It is therefore one of the principal objects of the invention to provide a non-destructive fluorescence X-ray spectrometry method and apparatus in which the spectral analysis of each elemental component is determined simultaneously, most desirably for gold, silver and platinum objects. A further object is to provide such a method and apparatus which would be integrated with an XRF analyzer and act as closed-loop, "all-in-one", single system, relatively compact, and would be effectively operated with relatively little or no formal training by its operator.

A related object is to combine both qualitative and quantitative test results (including sample weight and assay) with current precious metals market prices obtained via an Internet connection, whereby a near-immediate valuation (pricing) decision may be made by the system based on an algorithm contained within the system's "artificial intelligence" or "expert systems" software.

A further object is to provide a method and apparatus of assay and valuation which can record each step in the process of analysis and pricing such that both an electronic data record and a printed data record are created, and optionally including both a digital image of the object, and a printed quote of the offered price (if any) which may be retained by both the operator and the customer for future reference.

A related object is to provide means for electronically linking the data records thus created to a central database for the purpose of building artificial intelligence queries for existing library expansion as well as data that can further be reference by other commercial applications such as insurance underwriting, loss prevention, law enforcement, estate appraisal and resale services, and many similar applications.

A DESCRIPTION OF THE DRAWINGS

Figure 2:
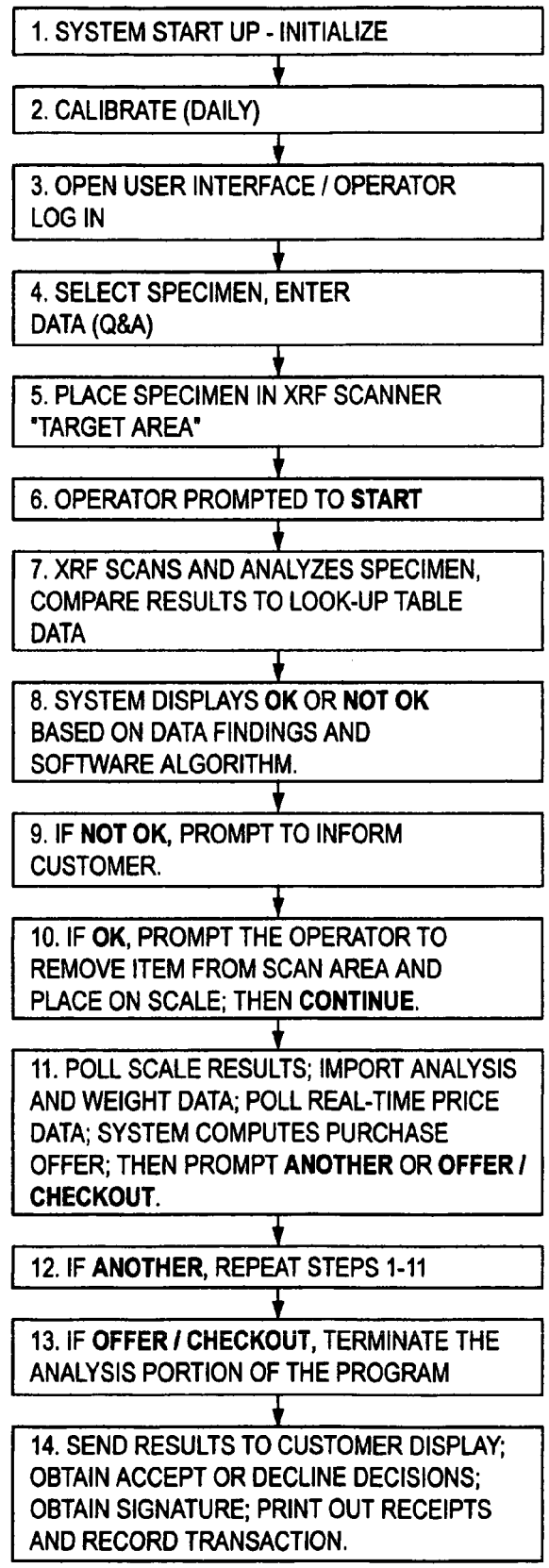

In the drawings,

FIG. 1 is a schematic illustration of the physical elements of a preferred embodiment of the present invention; and FIG. 2 is a schematic flow diagram illustrating the operation of the preferred embodiment of FIG. 1

A SUMMARY OF THE INVENTION

The objectives of the invention are achieved through the integration of the following basic elements: a commercially available XRF (X-Ray Technology) analyzing tester such as the "DELTA Precious Metals Handheld XRF Analyzer" or "GoldXpert Countertop XRF" marketed by Olympus Corporation, a touch tablet device or personal computer, and commonly available peripheral devices including a digital scale and a serial or USB compatible printer. The operation of either of the above mentioned XRF analyzers (as well as many several other models offered by previously cited manufacturers) is more fully described in the above-mentioned U.S. Pat. No. 5,062,127, the substance of which is incorporated herein by reference.

The objectives of the invention are accomplished by combining the foregoing equipment with a dedicated electronic user input-output interface using what is known in the art as "artificial intelligence" or "expert systems" software in accordance with the present invention. Because the system employs automatic testing procedures and computer-controlled technology, the system is capable of very high rates of data output, being necessary to quickly and economically analyze each sample and produce a printed record of the results.

According to the invention, even an untrained operator is quickly guided through a series of simple steps, characterized by "ease-of-use" technology, to determine the chemical makeup of a supposed precious metal sample. Additionally, the system of the invention also guides the operator through a series of questions to elicit answers which aid the system in determining more accurately the principal chemical and physical properties of the sample through the application of an artificial intelligence sorting and classifying process. After the system determines, through scanning, that the sample is a desirable item, it guides the user through the further steps of weighing (and optionally photographing) the sample, and then assaying its current market value using real-time market data.

The system of the invention has the further advantage of being able to quickly compare each sample, by using its test data, with pre-existing libraries of precious metals standards. In the case of jewelry, coins and precious metals, the system can compare the sample item with previously tested or otherwise known items of a similar nature.

An added advantage of the invention is that the system is capable of maintaining and using a large database of information. The system's software is capable of recording and maintaining detailed information from each item's analysis, and can keep detailed records of all items scanned. Such data desirably includes such elements as a time/date stamp, a geographic location stamp, a digital images of the specimen, and valuation data based on current precious metal market quotations.

Another major advantage of the invention is that the system is capable of providing fast and accurate results in a format that is completely transparent both to the user, and to the seller or customer. The system can display test results in real-time as each item is scanned, allowing the customer to view the system's valuation summary. It also offers interactive capability for the customer to accept or decline a cash offer for each item either individually or as a group or package. The customer thereby is likely to gain a higher degree of confidence and trust in the process, and will be enabled to make an educated decision whether to accept or decline a purchase offer as presented by the system.

DETAILED DESCRIPTION OF THE INVENTION

Turning to FIG. 1, there is shown in schematic form the principal physical elements of equipment as utilized in the invention. The invention is centered around a commercially available x-ray analyzer, which in the illustrated embodiment is, by way of example and not limitation, an Olympus "GoldXpert Countertop XRF". The components of the analyzer are combined within a case or chassis 10 which forms a self-contained unit for convenient and safe use.

In the illustrated embodiment, the components comprise a personal computer 11 with keyboard 12, a digital scale 13, an Olympus XRF analyzer 14, a touch-screen interface 15 associated with the analyzer 14, and a printer 16 for printing labels and/or customer receipts. A conventional keypad (not shown) may be substituted for the touch-screen interface 14.

The system may desirably be further augmented with a customer display 17 and customer input module or a combination thereof 18 to permit customers to observe the analysis and valuation process, and to interactively participate by indicating acceptance or rejection of whatever purchase offer the system of the invention computes based on the results of the analysis and artificial intelligent evaluation in the light of the then-prevailing market price for the principal metallic components of the sample or object.

The XRF operator interface 15 preferably includes an interactive touch screen and/or lighted push buttons which assist the operator in the process of analyzing and assigning a valuation to a particular sample.

According to the invention, software embodying a specialized process sequence (FIG. 2) is employed to collect the data from the XRF analyzer and its peripheral devices, including the user interface, and the digital scale. A digital camera (not shown) can be utilized as well. The software then compares this data with a precious metals database or library, preferable including an "expert systems" library compiled from previously analyzed samples.

As a function of this "artificial intelligence" data collection, the operator is first presented with a pre-scan question and answer interface, by which the operator interacts with the user interface module and software. This interaction includes answering certain important initial questions, such as what type of sample the item is, such as jewelry, a coin or some other metallic object. Depending on the type of item chosen, the system can prompt the operator to further define the object within one or more sub-categories. For example, in the case of jewelry, the system would offer choices including ring, necklace, broach, bracelet, etc., and depending on the operator's selection, may further prompt the operator with another sub-menu selection, such as whether gem stones are present or not. Additionally, the operator may be prompted to answer other questions such as "what precious metal does the object appear to be (i.e., gold or silver, etc.)", and "are there any obvious markings on the object (i.e., 10k, 14k, 18k, 925, HGE, STERLING . . . etc.)".

After accepting and storing the answers inputted by the operator in the pre-scan question-and-answer interface, the system then prompts the operator to place the sample object within the XRF analyzer's "target area" (14). Preferably, the system and offers specific instructions as to the placement and orientation of the object so that a flat surface of the sample is aligned optimally within the scanning window. For example, if the sample is a finger ring, the system would offer graphic illustrations as to how to orient the ring, such as to place the side or back solid edge of the ring flat on the surface in the middle of the analyzer's "target area", with any gem stones facing in the opposite direction.

Once the system is activated, and its software determines the sample's metallic and elemental composition, it is then able to provide the operator with a go/no-go purchase decision based on real-time data analysis and artificially intelligence algorithms. If the system's programmed decision is to make a purchase offer to the customer, then according to a further feature of the invention the system outputs an offering price to the customer based on sample composition, purity, weight, and real-time market price for that particular precious metal or combination of precious metals.

As yet a further advantage of the system, the analysis and test results, together with the offering price based on real-time market data, are displayed in real-time to the customer for review. This has the advantage of providing the customer with objective information with which to make a reasoned decision to either accept or decline the user's offer.

Then, as further feature of the invention, upon the customer's acceptance of the operator's purchase offer for one or more sample items, the system can immediately output by means of its associated printer a printed transaction order receipt, customer receipt, and even a set of self-adhesive labels to identify each sample lot or order.

In greater detail, the process of utilizing the invention includes the following steps, which are desirably (but not necessarily) followed in sequence:

1. System start up—initialization.
2. User calibration (daily).
3. Operator opens the user interface and logs onto the software system, thus recording date, time and operator.
4. Operator selects specimen, and enters data from pull-down menu on user interface, including type of specimen (jewelry, coins, flatware, raw metal or other), observed apparent type of metal (gold, silver, platinum), any observable markings on the specimen (such as 10k, 14k, 18k 925, HGE, Sterling, etc.), and purpose of analysis (cataloging, appraisal, buy/sell offer, etc.).
5. Upon prompting and instruction by the system, the operator opens lid to XRF scanner; places specimen in scanner "target area".
6. System prompts operator to press START.
7. XRF system analyzes the sample and compares metal analysis results to an internal look-up data library.
8. System displays "OK" or "NOT OK" to purchase item based on the software's algorithm that compares the systems scan results to the internal data look-up libraries as well as the collected data initially input by the operator for that specific item.
9. IF "NOT OK", system prompts operator to inform the customer that the item is not eligible for an offer, and to return it to the customer.
10. IF "OK", system prompts operator to remove the item and place it on the integrated scale; then CONTINUE.
11. On CONTINUE, the system polls the scale results, and the software imports both the analysis and weight data, using this data to compute a price based on the analysis, the weight, the real-time metals market price (polled via an external internet link) and a preset administrative formula based on "spot" market price of the subject precious metal. When this process is completed, the system outputs the analysis, weight and price results of each item analyzed to an external display viewable by the customer simultaneously as the system prompts the operator to select ANOTHER or OFFER/CHECKOUT.
12. If there are more items to analyze, the operator selects ANOTHER, which causes the system to repeat the above steps 1-11.
13. Once the last item is processed, the operator selects OFFER/CHECKOUT, which terminates the analysis portion of the program.
14. Upon selection of OFFER/CHECKOUT by the operator, the system displays all of the results, including each item's valuation and purchase offer (if any) in the order of analyzed. Each item is displayed on the operator's screen with an "Accept" and "Decline" selection box. This data can also be displayed on the customer-viewable external screen 17, and can then be printed out for the customer to accept with a signature. Alternately, a summary can be displayed on a touch-screen device input module 18 which the customer can select "ACCEPT ALL", "DECLINE ALL", or individually accept or decline each item separately by signing the designated location with a touch-screen stylus pen in a known manner.

In place of the external screen 17 and touch-screen device input module, an all-in-one touch screen display and interactive input module (not shown) can be substituted, of a kind which is commercially available and presently in use in many retail environments.

Preferably, after initialization and calibration, the system displays a LOG-IN Screen which will have two separate log-In options: an Operator Log-In and Administrator Log-In). Although both log-ins are preferably password protected, the Administrator Log-In will be available only to the owner or system manager, preferably with an extra layer of security protection such as a USB key fob device or biometrics signature, plus a password, to gain entry to the administrator's interface. Once logged in to the administration area, the administrator can initially be set up and thereafter maintained, including setting default percentages of market price in which the system uses to make its purchase offer calculations. Then, an operator may log in using his or her unique ID and password. Once the operator is logged in, and if recognized, the system displays system's beginning "Start/Ready" screen.

According to another feature of the invention, once a purchase transaction is signed and accepted by the customer, the system outputs from the printer 16 multiple copies of self-adhesive labels recording the transaction. For each sample for which a purchase transaction was completed, the user is then prompted to place into a sealable envelope or bag. The operator then applies a label to the envelope, another to the customer receipt, and another to the operator's daily log, thereby creating multiple permanent records of each transaction.

What is claimed is:

1. Apparatus for the metallurgical qualitative analysis (assay) and valuation of precious metals specimens such as jewelry or coins comprising a) a chassis having a sample stage for accepting a specimen,
b) a computer having a keyboard input means and an output display screen,
c) a digitizing scale having output means for transmitting weight information of a metals specimen to said computer,
d) an x-ray metals florescence (XRF) analyzer capable of being focused on the sample stage and specimen, and having output means for transmitting metals analysis information to said computer,
e) Internet communication means for obtaining current precious metals market prices and transmitting said price information to said computer,
f) software means for computer processing of said weight information, metals analysis information, and price information into a monetary valuation, and
g) display means for displaying said monetary valuation to an operator.

2. The apparatus of claim 1 for use in a commercial environment in which a customer has presented said specimen for purchase, and in which said software means includes an algorithm for deriving from said monetary valuation a proposed offering price to offer said customer.

3. The apparatus of claim 2 including a customer interface having a display screen for presenting said customer with said monetary valuation and said proposed offering price.

4. The apparatus of claim 3 including a customer input means for said customer indicate acceptance or rejection of said proposed offering price, software means for recording such acceptance or rejection, and output means for displaying a record of said acceptance or rejection.

5. The apparatus of claim 4 including printer means for creating at least one printed copy of said record of said transaction.

6. A method for the metallurgical qualitative analysis (assay) and valuation of precious metals specimens including jewelry and coins by a system operator, utilizing the apparatus of claim 1, comprising the steps of
a) selecting a specimen,
b) placing said specimen on said sample target area and focusing said x-ray florescence metals (XRF) analyzer on said specimen,
c) obtaining a metallurgical qualitative analysis (assay) from said analyzer and transmitting said metals analysis information to said computer,
d) weighing the specimen on the digitizing scale and transmitting the weight information of the specimen to said computer,
e) obtaining a current precious metal market price for the predominant metals in the specimen as determined by said analyzer,
f) computing a monetary valuation of said specimen as a function of its weight, metals analysis, and current precious metal market price, and displaying said valuation to said operator on said output display screen.

7. The method of claim 6 including the additional steps of
a) incorporating artificial intelligence and pre-determined "purchase/do not purchase" decision criteria into said monetary valuation to determine an offering price to said customer, and
b) displaying said offering price to said customer on a customer interface display screen.

8. The method of claim 7 including the additional step of allowing said customer to accept or reject said offering price using an output means for recording said acceptance or rejection, and recording said acceptance or rejection together with information as to weight, metallurgical qualitative analysis, date and price, together with buyer and seller information, and creating at least one printed record of said transaction.

* * * * *